United States Patent [19]

Krause et al.

[11] Patent Number: 4,468,355
[45] Date of Patent: Aug. 28, 1984

[54] PROCESS FOR MAKING 1-HYDROXY-ALKANE-1-PHOSPHONIC ACIDS

[75] Inventors: Werner Krause, Hürth; Werner Pieper, Erftstadt, both of Fed. Rep. of Germany

[73] Assignee: Hoechst Aktiengesellschaft, Fed. Rep. of Germany

[21] Appl. No.: 540,191

[22] Filed: Oct. 7, 1983

[30] Foreign Application Priority Data

Oct. 21, 1982 [DE] Fed. Rep. of Germany ....... 3238910

[51] Int. Cl.³ ................................................ C07F 9/38
[52] U.S. Cl. .............................. 260/502.4 R; 260/953
[58] Field of Search .................................. 260/502.4 R

[56] References Cited

U.S. PATENT DOCUMENTS 2,376,130  5/1945  Dickey et al. ............... 260/502.4 R
2,579,810 12/1951  Fields ........................... 260/502.4 R
3,202,692  8/1965  Weil et al. .................... 260/502.4 R
3,351,681 11/1967  Deinet .......................... 260/502.4 R
3,400,148  9/1968  Quinby ......................... 260/502.4 R
3,515,537  6/1970  Weil et al. .................... 260/502.4 R

FOREIGN PATENT DOCUMENTS 2555575  5/1973  Fed. Rep. of Germany ... 260/502.4 R

OTHER PUBLICATIONS

Conant et al., "J. Am. Chem. Soc.", vol. 44, (1922), pp. 2530–2536.

Primary Examiner—J. E. Evans
Attorney, Agent, or Firm—Connolly and Hutz

[57] ABSTRACT

The disclosure provides a novel process for making 1-hydroxyalkane-1-phosphonic acids by reacting an aldehyde with tetraphosphorus hexoxide.

6 Claims, No Drawings

PROCESS FOR MAKING 1-HYDROXY-ALKANE-1-PHOSPHONIC ACIDS

The present invention relates to a novel process for making 1-hydroxyalkane-1-phosphonic acids.

Hydroxyalkanephosphonic acids are, for example, commercially interesting complex formers.

Heretofore, they have been obtained by reacting an aldehyde with PCl$_3$. This process is however beset with considerable disadvantages as it is carried out in a plurality of stages with formation of various intermediates. In addition to this, corrosive hydrogen chloride and acetyl chloride which adversely affect the chlorine ion load of waste water, are obtained as by-products in stoichiometric quantities.

It is therefore highly desirable to have a process which avoids these adverse effects.

As has unexpectedly been found, these adverse effects are easy to avoid by reacting an aldehyde with tetraphosphorus hexoxide (P$_4$O$_6$), preferably in a molar ratio of at least about 4:1.

The aldehydes useful in the process of this invention are selected from compounds of the general formula

in which R stands for a halogen-substituted or unsubstituted alkyl, aryl, alkaryl or aralkyl group with 1 to 18 carbon atoms.

In carrying out the process of this invention it is possible for P$_4$O$_6$, which may be diluted with an inert organic solvent, to be admixed with metered proportions of aldehyde or for the aldehyde to be admixed dropwise with P$_4$O$_6$, which may be diluted with an inert organic solvent. Needless to say the aldehyde may also be diluted with an inert organic solvent.

The reaction should be effected at a temperature within the range 0° to 100° C., preferably 20° to 70° C.

Inasmuch as the crude reaction product may still contain polymeric or oligomeric material, it is good practice to hydrolyze this crude product so as to increase the yield. To this end, the crude product freed from solvent is hydrolyzed in an autoclave with the use of an excess of water at increased temperature and under increased pressure. The temperature selected for hydrolysis depends on the particular aldehyde used and normally varies between 100° to 250° C.

As more fully described in the following Examples, the present process provides a new route to phosphonic acids which are easy to produce in high yields by reacting tetraphosphorus hexoxide with an aldehyde.

Example 1

27.5 g P$_4$O$_6$ (0.125 mol) in 100 ml ethyleneglycoldimethylether was introduced under nitrogen into a multi-necked flask provided with a stirrer, reflux condenser, dropping funnel and internal thermometer and admixed dropwise within 30 minutes at 40°–50° C. with a solution of 60 g phenyl acetaldehyde (0.5 mol) in 50 ml ethyleneglycoldimethylether. After a postreaction period of 30 minutes at 50° C., the solvent was distilled off at a temperature of at most 120° C. 50 ml water was added to effect hydrolysis and the reaction product was heated for 3 hours to 180° C. in the autoclave. NMR-spectroscopy indicated that the crude product contained 85 weight % 1-hydroxy-2-phenylethane-1-phosphonic acid, 13.5 weight % H$_3$PO$_3$ and 1.5 weight % H$_3$PO$_4$.

Example 2

82 g (0.58 mol) decanal in 200 ml diethylether was introduced into an apparatus as described in Example 1 and 29 g (0.13 mol) P$_4$O$_6$ was added dropwise so that the reaction solution commenced boiling under reflux without additional supply of heat. After a post-reaction period of 2 hours at boiling temperature, the colorless, clear, slightly viscous solution was admixed dropwise with water until the exothermal reaction ceased to be recognizable. The solvent was removed at 60° C. under vacuum and 110 g of an amber-colored highly viscous product was obtained. To hydrolyze it, it was taken up in about 300 ml hot water and heated for 3 hours at 200° C. in the autoclave. Next, it was dissolved by the addition of acetone, filtered off from undissolved matter and evaporated.

The final product was a colorless wax which could be recrystallized from acetone to give 51 g (0.21 mol) 1-hydroxydecane-1-phosphonic acid in the form of analytically pure material. The melting point was 164° C. and the yield after recrystallization was 41%.

Example 3

59 g (0.4 mol) chloral in 100 ml ethyleneglycoldimethylether was introduced into an apparatus as described in Example 1 and heated to reflux temperature. Next, the solution was admixed dropwise within 15 minutes with 22 g (0.1 mol) P$_4$O$_6$. After a post-reaction period of 1 hour at 70° C., the whole was hydrolyzed with 15 ml water and concentrated under vacuum at temperatures of up to 100° C. 82 g of a highly viscous, slightly yellowish product was obtained. NMR-spectroscopy indicated that it was composed of:
 66 wgt % 1-hydroxy-2,2,2-trichloroethane-1-phosphonic acid,
 23 wgt % 1-hydroxy-2,2,2-trichloroethane-1-phosphonic acid, mono-(2,2,2-trichloro-1-phosphonoethyl)-ester, and
 11 wgt % phosphorous acid.

Example 4

27.5 g P$_4$O$_6$ (0.125 mol) in 100 ml ethyleneglycoldimethylether was introduced into an apparatus as described in Example 1 and a solution of 66.3 g benzaldehyde (0.625 mol) in 50 ml ethyleneglycoldimethylether was added dropwise within 30 minutes at 40°–50° C. After a post-reaction period of 1 hour at 50° C., the whole was hydrolyzed with 25 ml water and the solvent distilled off. $^{31}$P-NMR-spectroscopy indicated that the residue contained about 65% hydroxyphenylmethanephosphonic acid together with about 20% unidentified phosphonic acid derivatives as well as phosphorous acid and phosphoric acid.

Example 5

27.5 g P$_4$O$_6$ (0.125 mol) in 100 ml ethyleneglycoldimethylether was introduced into an apparatus as described in Example 1 and a solution of 43.5 g (0.75 mol) propionaldehyde in 50 ml ethyleneglycoldimethylether was added dropwise. After a post-reaction period of 10 minutes at 50° C., 10 ml water was added and the crude product was evaporated to dryness using a rotary evaporator. NMR-spectroscopy indicated that the crude product was composed of:

21 wgt % 1-hydroxypropane-1-phosphonic acid,
71 wgt % 1-hydroxypropane-1-phosphonic acid-mono (1-phosphono-propyl)-ester,
7 wgt % phosphorous acid,
1 wgt % phosphoric acid.

The crude product was further hydrolyzed and to this end an aqueous solution thereof was heated for 3 hours to 180° C. in the autoclave. The reaction product so obtained was composed as follows: ($^{31}$P-NMR)

82 wgt % 1-hydroxypropane-1-phosphonic acid,
9 wgt % 1-hydroxypropane-1-phosphonic acid mono-(1-phosphonopropyl)-ester,
7 wgt % phosphorous acid,
2 wgt % phosphoric acid.

We claim:

1. A process for making 1-hydroxyalkane-1-phosphonic acids, which comprises reacting an aldehyde with tetraphosphorus hexoxide (P$_4$O$_6$).

2. The process as claimed in claim 1, wherein the aldehyde and P$_4$O$_6$ are reacted in a molar ratio of at least 4:1.

3. The process as claimed in claim 1, wherein the aldehyde is a compound of the general formula

in which R stands for a halogen-substituted or unsubstituted alkyl, aryl, alkylaryl or aralkyl group with 1 to 18 carbon atoms.

4. The process as claimed in claim 1, wherein the reaction is effected at a temperature within the range 0° to 100° C.

5. The process as claimed in claim 1, wherein the crude reaction product is freed from solvent and hydrolyzed with the use of an excess of water under increased pressure and at increased temperature.

6. The process as claimed in claim 5, wherein the crude reaction product is hydrolyzed at temperatures between 100° and 250° C.

* * * * *